United States Patent
Peterson et al.

(10) Patent No.: US 9,907,648 B2
(45) Date of Patent: Mar. 6, 2018

(54) INTRAOCULAR LENS AND CARTRIDGE PACKAGING WITH LENS-LOADING FUNCTION

(75) Inventors: Rod T. Peterson, Tustin Ranch, CA (US); Mark S. Cole, Trabuco Canyon, CA (US); Robert D. Ott, Irvine, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 1102 days.

(21) Appl. No.: 11/563,621

(22) Filed: Nov. 27, 2006

(65) Prior Publication Data
US 2007/0095700 A1    May 3, 2007

Related U.S. Application Data

(62) Division of application No. 10/453,830, filed on Jun. 2, 2003, now Pat. No. 8,403,941.

(51) Int. Cl.
*A61F 2/16* (2006.01)

(52) U.S. Cl.
CPC .......... *A61F 2/1691* (2013.01); *A61F 2/1678* (2013.01)

(58) Field of Classification Search
CPC ............................ A61F 2/1678; A61F 2/1691
USPC ................................................ 623/6.11, 6.12
See application file for complete search history.

(56) References Cited

U.S. PATENT DOCUMENTS

| | | |
|---|---|---|
| 4,199,826 A | 4/1980 | Devereux |
| 4,402,396 A | 9/1983 | Graham |
| 4,763,650 A | 8/1988 | Hauser |
| 4,765,329 A | 8/1988 | Cumming et al. |
| 4,817,789 A | 4/1989 | Paul |
| 4,834,094 A | 5/1989 | Patton et al. |
| 4,836,201 A | 6/1989 | Patton et al. |
| 4,862,885 A | 9/1989 | Cumming |
| 4,919,130 A | 4/1990 | Stoy et al. |
| 4,976,716 A | 12/1990 | Cumming |
| 5,066,297 A * | 11/1991 | Cumming ..................... 606/107 |
| 5,123,905 A | 6/1992 | Kelman |
| 5,139,501 A | 8/1992 | Klaas |
| 5,171,241 A | 12/1992 | Buboltz et al. |

(Continued)

FOREIGN PATENT DOCUMENTS

| | | |
|---|---|---|
| EP | 0402138 | 12/1990 |
| FR | 2833154 A1 | 12/2001 |

(Continued)

OTHER PUBLICATIONS

U.S. Appl. No. 10/453,830, filed Jun. 2, 2003.
U.S. Appl. No. 11/563,603, filed Nov. 27, 2006.

*Primary Examiner* — Gregory Anderson
*Assistant Examiner* — Sarah Simpson
(74) *Attorney, Agent, or Firm* — Abbott Medical Optics Inc.

(57) ABSTRACT

A lens and cartridge packaging system and method of use which simplify the removal and transfer of an IOL to an IOL insertion device is disclosed. The packaging system enables a user to easily load an IOL into a cartridge without the use of forceps. In addition, the packaging system also allows a user to fold and insert the IOL into a cartridge without damaging the IOL and/or compromising IOL sterility. In addition, the related methods of use minimize and/or eliminate damage to the IOL during unpackaging, folding, transfer and loading procedures.

19 Claims, 12 Drawing Sheets

(56) References Cited

U.S. PATENT DOCUMENTS

| | | | |
|---|---|---|---|
| 5,176,686 A | 1/1993 | Poley | |
| 5,199,559 A | 4/1993 | Dark | |
| 5,281,227 A | 1/1994 | Sussman | |
| 5,356,006 A | 10/1994 | Alpern et al. | |
| 5,578,042 A * | 11/1996 | Cumming | 606/107 |
| 5,582,614 A * | 12/1996 | Feingold | A61F 2/1678 |
| | | | 606/107 |
| 5,647,372 A | 7/1997 | Tovey et al. | |
| 5,752,923 A | 5/1998 | Terwilliger | |
| 5,800,441 A | 9/1998 | Polla et al. | |
| 5,947,974 A | 9/1999 | Brady et al. | |
| 6,048,347 A | 4/2000 | Erdman | |
| 6,129,733 A | 10/2000 | Brady et al. | |
| 6,143,000 A | 11/2000 | Feingold | |
| 6,183,513 B1 | 2/2001 | Guenthner et al. | |
| 6,228,094 B1 * | 5/2001 | Erdman | A61F 2/1664 |
| | | | 606/107 |
| 6,336,932 B1 | 1/2002 | Figueroa et al. | |
| 6,355,046 B2 | 3/2002 | Kikuchi et al. | |
| 6,386,357 B1 * | 5/2002 | Egawa | 206/5.1 |
| 6,406,481 B2 | 6/2002 | Feingold et al. | |
| 6,447,519 B1 * | 9/2002 | Brady et al. | 606/107 |
| 6,468,282 B2 | 10/2002 | Kikuchi et al. | |
| 6,471,708 B2 * | 10/2002 | Green | 606/107 |
| 6,497,708 B1 | 12/2002 | Cumming | |
| 6,497,709 B1 | 12/2002 | Heath | |
| 6,500,181 B1 | 12/2002 | Portney | |
| 6,503,275 B1 | 1/2003 | Cumming | |
| 6,786,911 B2 | 9/2004 | Mitomo et al. | |
| 6,960,200 B2 | 11/2005 | Shapeton et al. | |
| 7,172,104 B2 | 2/2007 | Scirica et al. | |
| 2001/0004052 A1 | 6/2001 | Sakanishi | |
| 2001/0041897 A1 | 11/2001 | Feingold et al. | |
| 2002/0077633 A1 | 6/2002 | Kikuchi et al. | |
| 2002/0082609 A1 * | 6/2002 | Green | A61F 2/1691 |
| | | | 606/107 |
| 2002/0103490 A1 | 8/2002 | Brady | |
| 2002/0108875 A1 | 8/2002 | Feinberg et al. | |
| 2003/0209452 A1 * | 11/2003 | Mitomo et al. | 206/5.1 |
| 2004/0059343 A1 | 3/2004 | Shearer et al. | |
| 2004/0238392 A1 | 12/2004 | Peterson et al. | |
| 2005/0163686 A1 | 7/2005 | Bettenhausen et al. | |
| 2006/0200167 A1 | 9/2006 | Peterson et al. | |
| 2007/0060925 A1 | 3/2007 | Pynson | |
| 2007/0123980 A1 | 5/2007 | Peterson et al. | |

FOREIGN PATENT DOCUMENTS

| | | |
|---|---|---|
| JP | 08-507457 | 8/1996 |
| JP | 2001104363 A2 | 4/2001 |
| WO | WO 9420027 | 9/1994 |
| WO | 97/20661 | 5/1998 |
| WO | WO 9820819 A1 | 5/1998 |
| WO | 98/26189 | 12/1998 |
| WO | WO 9929267 | 6/1999 |
| WO | 03049645 A2 | 6/2003 |
| WO | 2004018175 | 6/2004 |

\* cited by examiner

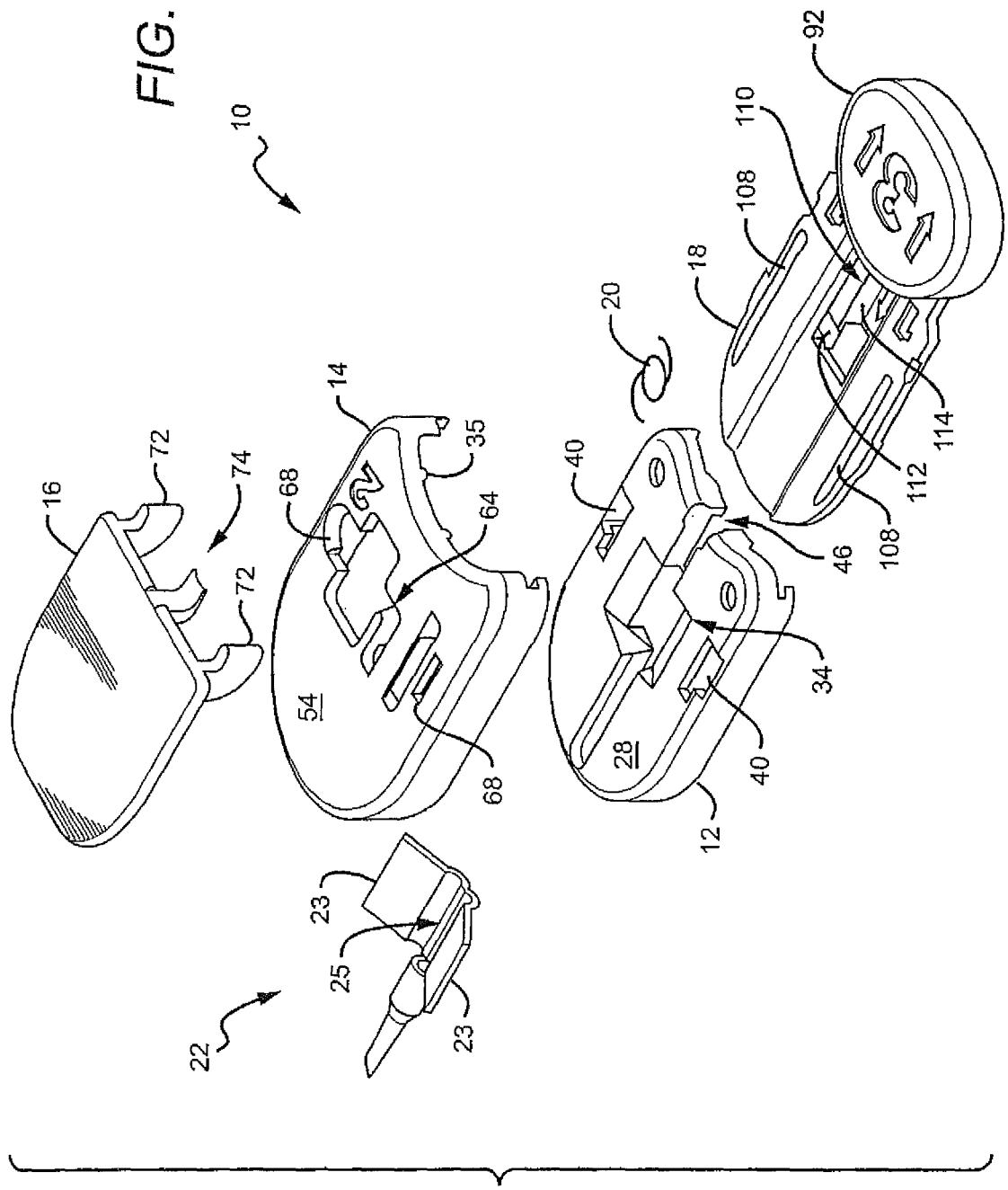

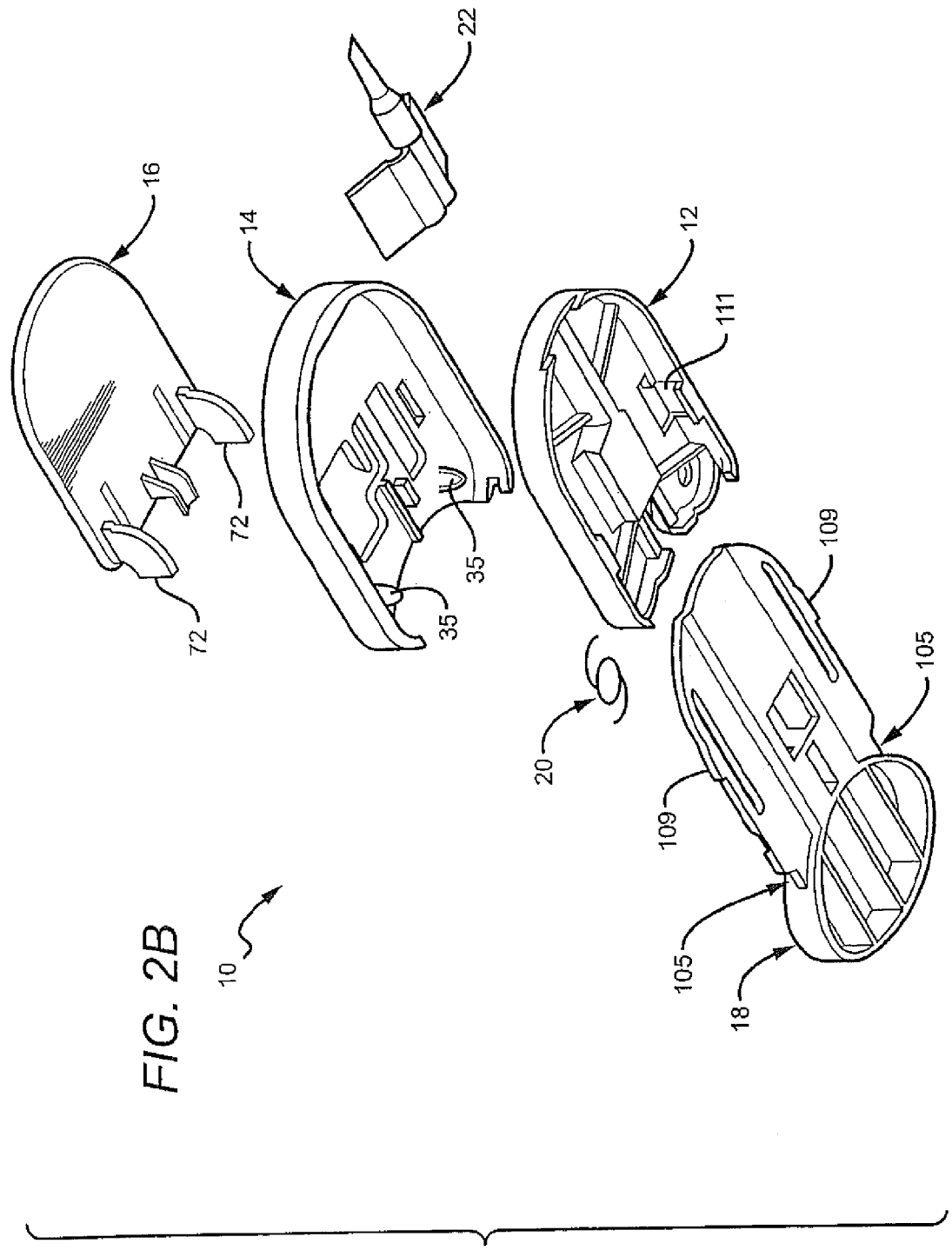

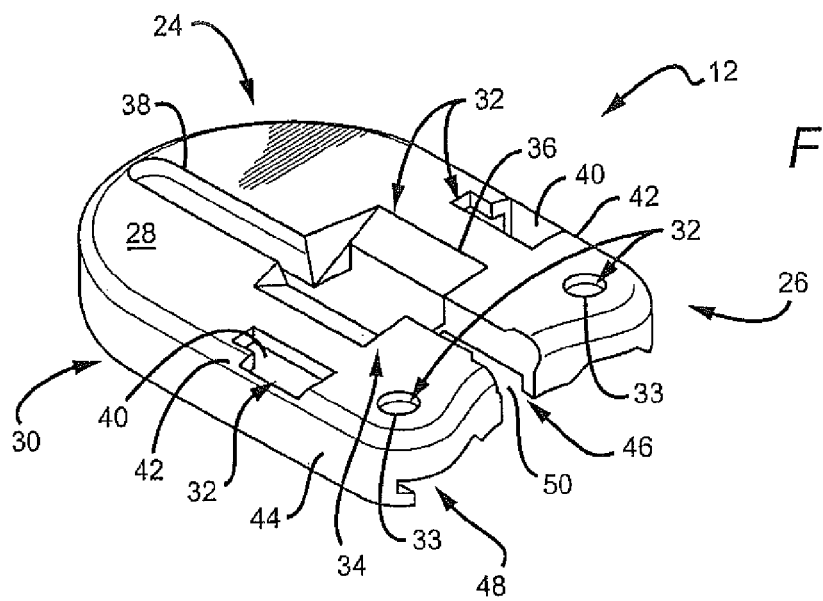
FIG. 3
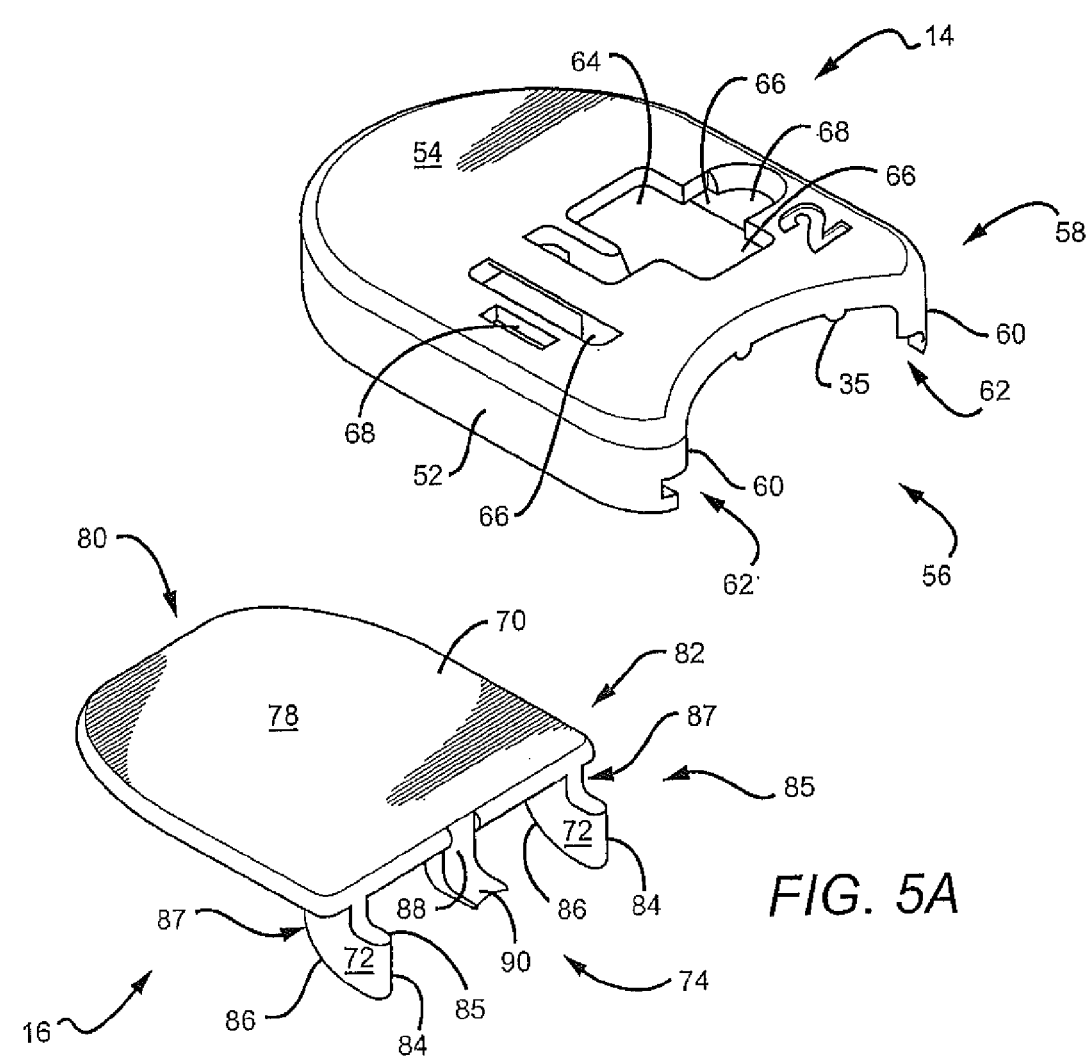
FIG. 4
FIG. 5A

INTRAOCULAR LENS AND CARTRIDGE PACKAGING WITH LENS-LOADING FUNCTION

RELATED APPLICATIONS

This application is a divisional application of U.S. patent application Ser. No. 10/453,830, filed Jun. 2, 2003.

BACKGROUND OF THE INVENTION

It is estimated that at least about 42% of Americans between the ages of 52 and 64 and 73% of Americans between the ages of 65 to 74 get cataracts. A cataract is a clouding of the eye's lens that impairs a person's vision and, if left untreated, causes blindness. As a result, each year approximately 1.4 million people in the United States alone undergo cataract surgery, whereby the clouded lens is removed and replaced with an intraocular lens (IOL) implant.

A typical IOL includes an optic or lens body for focussing light toward the retina of the eye. In addition, the IOL also includes one or more fixation members or haptics for securing the IOL in the desired position within the chamber of the eye. The IOL is implanted directly into the eye through a small incision formed in the ocular tissue of the eye. To fit through this small incision, modern IOLs are designed to be deformed, e.g., rolled, folded or the like, to a relatively small profile and then allowed to return to their original shape within the eye.

A useful technique for inserting an IOL into the eye includes use of an IOL injector or cartridge. Conventional IOL cartridges include a load chamber which is connected to an injection tube. The load chamber further includes an openable first lumen for receiving the IOL. Closure of this first lumen folds the IOL and maintains the IOL in a folded state. The injection tube includes a small diameter distal tip which is insertable into the incision within the eye. The IOL is transferable from the load chamber through the injection tube and into the eye.

In general, the IOL is provided to the surgeon in packaging, such as a vial, plastic blister package, or other container for maintaining the IOL in a sterile condition. The IOL is removed from the packaging and placed on the open load chamber prior to insertion into the patient's eye. The packaging protects the IOL during handling and transportation to the surgical site and maintains the sterility of the IOL prior to use.

The technique of removing the IOL from the packaging and transferring it to the load chamber is usually accomplished with a pair of forceps or similar device. Any covering of the packaging is removed so that the IOL is exposed in its container. Insertion forceps are used to remove the IOL from the packaging and subsequently fold the IOL to a reduced size for insertion into the eye. Alternatively, the forceps are used to physically remove the IOL from the packaging and place it on the load chamber of the cartridge. Whether folding the IOL or simply loading it into the cartridge, this step requires particular manual dexterity and surgical skills.

In this regard, a variety of problems may arise when removing the IOL from its packaging, manually folding the IOL and/or placing the IOL into an insertion device. For example, if proper care is not exercised during manipulation of the IOL, the IOL can be dropped and/or damaged. In addition, the IOL can be damaged if improperly folded or loaded into the cartridge and insertion device. Further, IOL sterility may be compromised if the IOL is not handled properly during the unpacking and loading procedures, thereby requiring the IOL to be discarded.

In view of the above, there is a need for a packaging system and method of use which simplify the removal and transfer of the IOL to the IOL insertion device. In particular, it is desirable that the packaging system enables a user to easily load an IOL into a cartridge without the use of forceps. Such a system should also allow a user to fold and insert the IOL into a cartridge without damaging the IOL and/or compromising IOL sterility, in addition to generally permitting it to be visible to the doctor prior to use. In addition, the related methods of use should minimize and/or eliminate damage to the IOL during unpackaging, folding, transfer and loading procedures.

SUMMARY OF THE INVENTION

In general, the present invention contemplates a lens and cartridge packaging system that includes a lens loading function, and satisfies related doctor and/or support staff needs.

The present invention further contemplates a device to store and transfer an intraocular lens. The device comprises an intraocular lens and a tray having an aperture, wherein the intraocular lens is housed within a portion of the aperture and wherein another portion of the aperture is configured to house a lens cartridge. The device also includes a push-rod in communication with the tray, wherein the push-rod causes controlled movement of the intraocular lens within the device. In addition, the device also includes a lock in communication with the tray and the push-rod, wherein the lock prevents unintentional movement of the push-rod and intraocular lens within the device.

The present invention also contemplates a method of storing an intraocular lens and transferring said intraocular lens to a lens cartridge for use in a delivery device. The method comprises providing a packaging device housing an intraocular lens and a lens cartridge within a tray of the packaging device, wherein the packaging device further comprises a push-rod in communication with the tray and a lock in communication with the tray and the push-rod. The method also includes removing the lock to enable movement of the push-rod and distally advancing the push-rod to transfer and secure the intraocular lens within a loading zone of the lens cartridge. Finally, the method includes proximally retracting the push-rod to release the intraocular lens and the lens cartridge, and removing the lens cartridge from the packaging device, wherein the lens cartridge now contains the intraocular lens.

BRIEF DESCRIPTION OF THE DRAWINGS

Other features and advantages of the present invention will be seen as the following description of particular embodiments progresses in conjunction with the drawings, in which:

FIG. 1 is an exploded perspective view of an embodiment of a lens packaging system in accordance with the present invention;

FIG. 2B is another exploded perspective view of the underside of an embodiment of a lens packaging system in accordance with the present invention;

FIG. 3 is a perspective view of an embodiment of a tray of a lens packaging system in accordance with the present invention;

FIG. 4 is a perspective view of an embodiment of a lid of a lens packaging system in accordance with the present invention;

FIG. 5A is a perspective view of an embodiment of a lock of a lens packaging system in accordance with the present invention;

DETAILED DESCRIPTION OF THE PREFERRED EMBODIMENTS

Figure 2A:
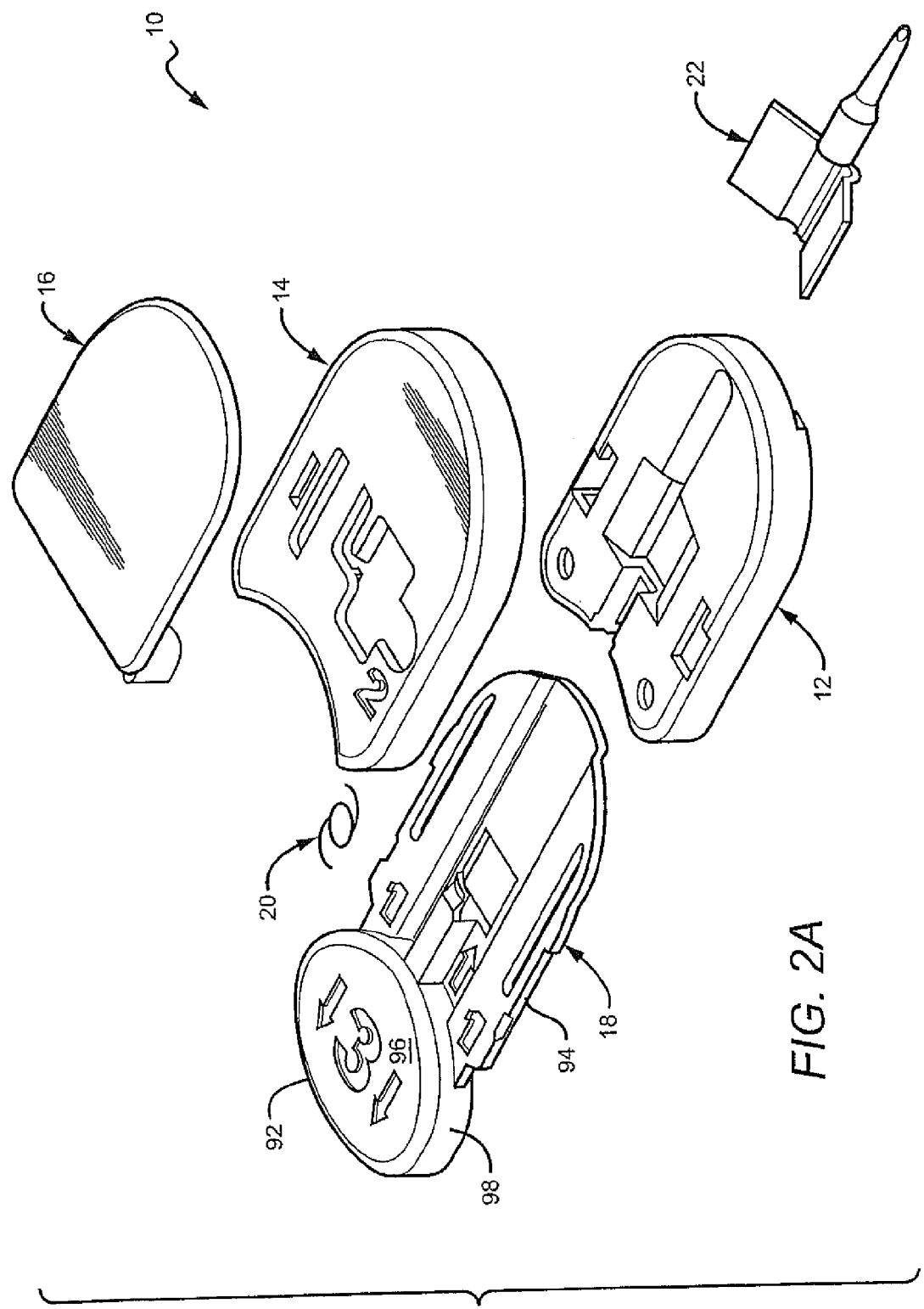
FIG. 2A is another exploded perspective view of an embodiment of a lens packaging system in accordance with the present invention.

Referring now to the drawings, wherein like reference numerals designate identical or corresponding parts throughout the several views and embodiments, a lens packaging system 10 in accordance with the present invention, shown in FIGS. 1, 2A and 2B, includes a tray 12, a lid 14, a lock 16, and a push-rod 18. The tray 12 is configured to hold and store a foldable IOL 20 and a cartridge 22. In this regard, the IOL 20 and cartridge 22 are held within the tray 12 via the lid 14, lock 16 and push-rod 18. In addition to securing the IOL 20 and cartridge 22, the lock 16 also serves as a means to secure the push-rod 18 during shipment/storage of the packaging system 10 and, thereby, prevent accidental activation of the push-rod mechanism.

In general, the packaging system 10 of the present invention may be fabricated as a disposable, single-use component or a reusable, multi-use component. As such, a variety of materials may be used to fabricate the tray 12, lid 14, lock 16 and push-rod 18 of the packaging system 10. These materials include, but are not limited to, plastics, metals (such as stainless steel, aluminum or titanium), ceramics and the like, including combinations thereof. By way of illustrative example, with no limitation being intended or implied, the tray 12 is fabricated from polypropylene, and the lid 14, lock 16 and push-rod 18 are fabricated from polycarbonate.

Referring now to FIGS. 2A, 2B and 3, the packaging system 10 will be described in greater detail. In particular, in one embodiment of the packaging system 10, the tray 12 includes a distal end 24, a proximal end 26, a half-oval shaped top surface 28 and a sidewall 30. As shown in FIGS. 2A, 2B and 3, the distal end 24 of the tray 12 is rounded or curved to conform to the curved portion of the half-oval shaped top surface 28. The proximal end 26 of the tray 12 is also slightly curved or rounded and arches in the same direction as the distal end 24 of the tray 12. In general, the proximal end 26 of the tray 12 is configured to accommodate the push-rod 18 of the packaging system 10, as described in further detail below. Alternatively, in other embodiments (not shown), the distal and proximal ends 24, 26 of the tray 12 are arched in opposite directions. Furthermore, in certain embodiments, the distal and proximal ends 24, 26 of the tray 12 are angled to form a portion of a square, rectangle, triangle, quadrilateral, regular and/or irregular-shaped form.

As illustrated in FIG. 3, the distal and proximal ends 24, 26 of the tray 12 also correspond to the distal and proximal ends of the tray's top surface 28. The top surface 28 of the tray 12 is generally planar or flat and includes one or more indentations and/or apertures 32 formed therein. The proximal-most apertures 33 are formed as two round holes in the top surface 28 of the tray. These apertures or holes 33 are configured to accommodate the alignment pins of the lid 14, as explained in further detail below.

The remaining indentations and/or apertures 32 are configured to accommodate a lens 20 and lens cartridge 22, or similar lens holding and/or folding device, and guide elements or posts, for aligning the lid 16 and/or push-rod 18 of the packaging system 10. In the embodiment of the packaging system 10 illustrated in FIG. 3, the center aperture 34 is approximately cross-shaped and includes a wide transverse slot 36 that intersects a narrow, elongate longitudinal slot 38 extending approximately from the proximal end 26 to the distal end 24 of the tray. The center aperture 34 further includes various chamfers and ridges within each slot 36, 38, which provide additional support and stability for the lens cartridge 22. As such, during storage and/or prior to use of the system 10, it is the narrow, distal section of the longitudinal slot 38 together with the wide transverse slot 36 that house the cartridge 22, whereas the narrow, proximal section of the central aperture's longitudinal slot 38 (also known as the lens platform) houses the IOL 20.

Adjacent the center aperture 34 are two additional longitudinal side-slots 40. Each side-slot 40 is positioned on either side and in alignment with the wide transverse slot 36 of the center aperture 34. In general, the side-slots 40 are approximately L-shaped and extend along the longitudinal axis near the side edges 42 of the tray 12. The side-slots 40 are designed to accommodate the guideposts of the lock 16, as described in further detail below.

Integral with the top surface 28 of the tray 12 is a sidewall 44. The sidewall 44 extends along the perimeter of the top surface 28 and forms a hollow cavity beneath the top surface 28 of the tray 12. As best seen in FIG. 3, an opening 46 extends along a portion of the sidewall 44 located near the tray's proximal end 26. In particular, the opening 46 includes a first portion 48 and a second portion 50, wherein the first portion 48 of the opening 46 extends along a transverse, proximal section of the tray's sidewall 44. The second portion 50 of the opening 46 forms a longitudinal slot that is continuous with the first portion 48 and extends in a distal direction along the top surface 28 of the tray 12. In particular, the second portion 50 of the opening 46 merges with the cartridge-shaped aperture/indentation 34 of the top surface 28. In general, the opening 46 is configured to accommodate the push-rod 18 of the packaging system 10, as described in further detail below.

As referenced above, the packaging system 10 of the present invention also includes a lid 14 configured to cover at least a portion of the top surface 28 and sidewall 44 of the tray 12. In this regard, as shown in FIGS. 2A, 2B and 4, the shape of the lid 14 is nearly identical to the shape of the tray 12. However, as best seen in FIG. 4, the sidewall 52 of the lid 14 does not extend completely around the perimeter of the lid's top surface 54 but, rather, includes a generally rectangular-shaped gap or aperture 56 near the proximal end 58 of the lid 14. In addition, each vertical edge 60 of the sidewall 52 that frames the gap or aperture 56 further includes at least one notch 62, which is continuous with the aperture 56 near the proximal end 58 of the lid 14. As explained in further detail below, the lid's aperture and notches 56, 62, which are in direct alignment with the longitudinal slot 46 of the tray 12, are generally configured to accommodate the push-rod 18 when fully advanced during transfer of the IOL 20 into the cartridge 22.

In addition to differences in the sidewalls 44, 52, there are also slight differences in the apertures/indentations formed in the top surfaces 28, 54 of the tray 12 and lid 14. In particular, as shown in FIG. 4, the proximal end of the lid's top surface 54 does not include apertures or indentations, as does the tray 12. However, as best seen in FIG. 2B, the underside of the lid, near its proximal end, includes one or more alignment pins 35. As explained above, these alignment pins 35 are configured to seat within the holes 33 of the tray 12 and, thereby, align and secure the lid 14 onto the tray 12 of the device 10.

Referring to FIGS. 1, 2A, 2B and 4, a central window 64 and indentations or tabs 66 are formed in the top surface 54 of the lid 14 and are generally aligned with the center aperture 34 of the tray 12. When a cartridge 22 is seated within the center aperture 34 of the tray 12, the central window 64 and tabs 66 allow portions of the cartridge 22 to be exposed, with the remaining portions of the cartridge 22 covered and secured by the lid 14. As such, the lid 14 functions to not only secure the cartridge 22 within the packaging system 10 during storage and/or use of the system/device 10, but also to maintain the cartridge 22 in an open position, by supplying sufficient force to the cartridge's wings 23, to expose the loading zone 25 of the cartridge 22. With the loading zone 25 exposed and in direct alignment with the lid's central window 64, a user of the packaging system 10 may easily apply a viscoelastic gel or viscoelastic surgical device (VSD), or lubricant (not shown) to the cartridge 22.

In general, a VSD is injected into the eye to help maintain the shape of ocular structures and as a lubricant/coating to minimize trauma from surgical instruments and implants. In addition, viscoelastic is also used in cartridges as a form of lubricant to aid in the passing of the IOL through the cartridge. Further, the viscoelastic also prevents air bubbles from being delivered into the eye with the IOL, which would obstruct the surgeon's view during the IOL insertion procedure.

As with the tray 12, the lid 14 of the packaging system 10 also includes one or more longitudinal side-slots 68. Each side-slot 68 is positioned on either side of the indentations/ tabs 66 and are designed to accommodate the guideposts of the lock 16. To further understand the interaction between the side-slots 68, 40 of the lid 14 and tray 12 and the guideposts of the lock 16, it is instructive to first describe the lock 16 of the present invention. For this purpose, reference is made to FIGS. 2A, 2B, 5A, 5B, 6 and 7.

Figure 5B:
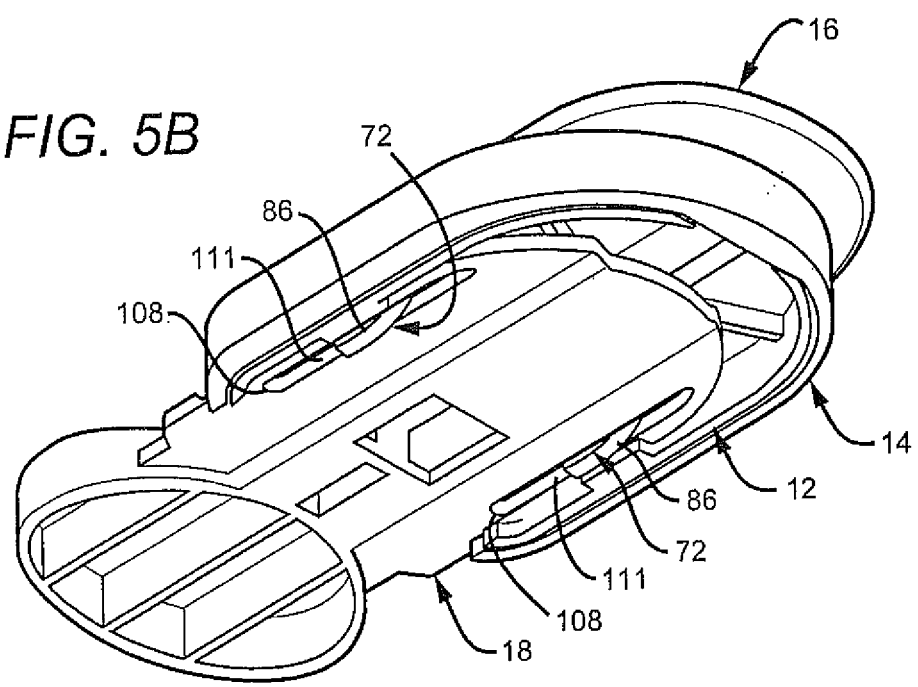
FIG. 5B is a perspective view of the underside of an embodiment of a lens packaging system in accordance with the present invention.
Figure 6:
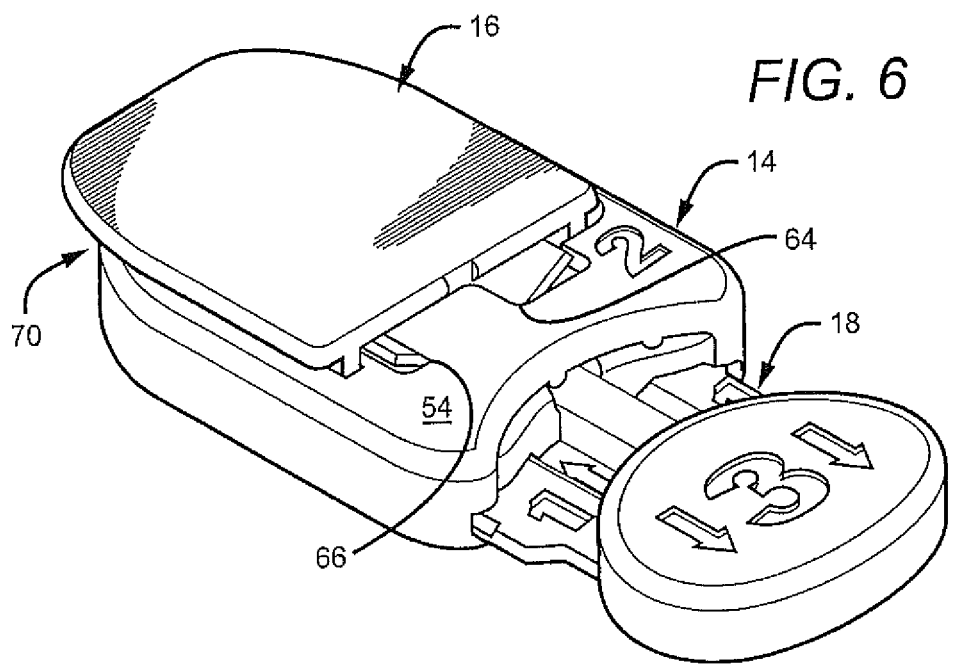
FIG. 6 is a perspective view of an embodiment of a lens packaging system in accordance with the present invention.
Figure 7:
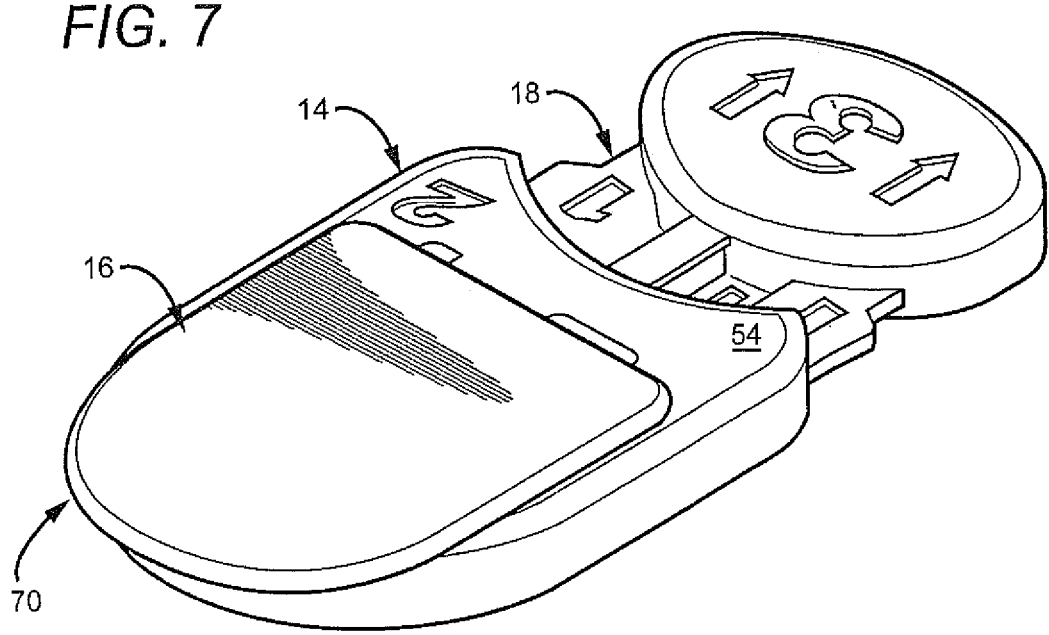
FIG. 7 is an alternate perspective view of the lens packaging system of FIG. 6.

FIG. 5A depicts an embodiment of the lock 16 as used in the packaging system 10 of the present invention. The lock 16 includes a generally planar or flat body 70, two guideposts 72 and an IOL support 74. The body 70 of the lock 16 further includes a top surface 78 and a bottom surface (not shown) that are shaped similar to the top surfaces 28, 54 of the tray 12 and lid 14. In particular, the body 70 is configured in a half-oval shape that includes a rounded or curved distal end 80 and a relatively straight or linear proximal end 82. As best seen in FIGS. 6 and 7, the body 70 of the lock 16 is sized to cover a substantial portion of the top surface 54 of the lid 14 and, in particular, at least a portion of the central window and indentations of the lid 14.

The guideposts or guide elements 72 of the lock 16 are also relatively planar or flat, but lie in vertical planes that are perpendicular to the plane of the lock's bottom surface. Each guidepost 72 is configured approximately in the shape of a quarter-circle and includes a first or longitudinal straight edge (not shown), a second or vertical straight edge 84 and a rounded edge 86. As shown in FIGS. 5A and 5B, the first straight edge of each guidepost 72 extends in a longitudinal direction along the bottom surface of the lock 16. The second edge 84 of each guidepost 72 is positioned at approximately a ninety-degree angle from the first straight edge and near the proximal end 82 of the lock 16. However, a notch 85 is formed in the portion of the guidepost 72 where the first and second edges 84 intersect. The notch 85 forms a type of neck or stem region 87 on the guidepost 72 and is configured to seat within the narrow portion of the L-shaped slot 40 of the tray 12, as explained in further detail below. The remaining rounded edge 86 of the guidepost 72 connects the first and second edges 84 of the guidepost 72, thereby forming its generally quarter-circle shape. As referenced above, each guidepost 72 is sized to fit within the longitudinal side-slots 40, 68 of the tray 12 and lid 14. As such, the guideposts 72 are parallel to each other and symmetrically positioned near the side edges of the lock 16, which generally correspond to the side edges of the lid 12 and tray 14.

As shown in FIGS. 5A, 5B, 6 and 7, the lock 16 of the packaging system also includes an IOL support 74, which is positioned near the straight proximal end 82 of the lock 16. The IOL support 74 is generally L-shaped and includes a first component 88 and a second component 90. The first component 88 of the IOL support 74 extends in a vertical direction, similar to the second edge 84 of the guideposts 72, and is attached to the body 70 of the lock 16. The second component 90 of the IOL support 74 extends in a proximal direction along the longitudinal axis of the device 10 and is configured to fit near the loading zone of the cartridge 22. In general, the IOL support 74 buttresses and carries the distal edge of the IOL 20.

As noted in the Background of the Invention as set forth above, there is a need for a packaging system 10 that enables a user to easily transfer an IOL 20 into a cartridge 22 without damaging the IOL 20 or compromising its sterility. As the present invention substantially eliminates these undesirable characteristics, it is instructive to particularly describe the push-rod 18 that reliably drives or transfers the IOL 20 into the cartridge 22 white maintaining IOL sterility. For this purpose, reference is made to FIGS. 2A, 2B and 8.

Figure 8:
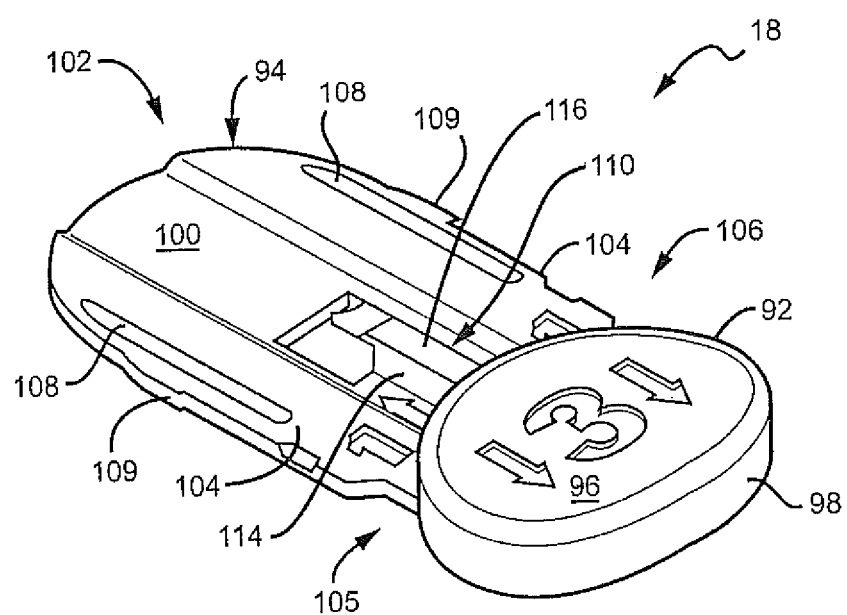
FIG. 8 is a perspective view of an embodiment of a push-rod of a lens packaging system in accordance with the present invention.

FIGS. 2A, 2B and 8 illustrate one embodiment of the push-rod 18, which includes a oval-shaped handle 92 in communication with a half-oval shaped slide 94. In general, the handle 92 of the push-rod 18 includes a circular pushing surface 96 and a sidewall 98 that extends around the perimeter of the surface 96. The sidewall 98 provides additional structural support and gives added dimension to the handle 92 to enable a user to securely and controllably grip the push-rod 18 of the system. As best seen in FIGS. 2A and 2B, the half-oval shaped slide 94 is connected to the handle 92 of the push-rod 18 via the sidewall 98.

As with the lock 16 of the present invention, the slide 94 of the push-rod 18 includes a generally planar or flat body 100 having a top surface and a bottom surface that are shaped similar to the top surfaces 28, 54 of the tray 12 and lid 14. In this regard, the slide 94 of the push-rod 18 is configured in a half-oval shape that includes a rounded or curved distal end 102, two side-edges 104 and a proximal end 106 that follows the outline-shape of a portion of the sidewall 98. Overall, the slide 94 is sized to fit through the opening 46 of the sidewall 44 and within the tray 12 of the packaging system 10

As best seen in FIGS. 2B, 4 and 8, one or more indentations 105 are located along the side-edges 104 and near the proximal end of the planar body 100 of the push-rod 18. These indentations 105 are configured to bypass the portion or section of the lid's sidewall 52 that surrounds or frames the lid's notches 62. In particular, during storage, the indentations 105 of the push-rod 18 are positioned proximal to and outside of the notches 62 of the lid 14. As such, the wider, non-indented section of the push-rod 18 is seated within the notches 62 so that the lid 14 cannot be removed from the system or device 10. However, when the push-rod 18 is actuated or advanced distally, the indentations 105 fall into alignment with the notches 62, thereby allowing lid removal.

Referring to FIGS. 2B, 5B and 8, each side-edge 104 of the slide 94 further includes one or more detents 109 which are configured to interact with the detent-slots 111 of the tray 12. Adjacent the detents 109 is a groove or slot 108 that extends along a longitudinal length of the slide 94. The grooves 108 are configured to accommodate the guideposts 72 of the lock 16 when the push-rod 18 is in a fully retracted or non-actuated position, as shown in FIG. 5B. In addition, the grooves 108 also allow sufficient inward movement of the side-edges of the push-rod 18 to enable the detents 109 to pop out of the detent-slots 111 and travel along the inside sidewall of the tray 12 during device activation.

In this regard, prior to device activation, the detents 109 of the push-rod 18 are seated within the detent-slots 111 of the tray 12. To prevent unintentional device activation by dislodging the detents 109 from the detent-slots 111 via distal sliding movement of the push-rod 18, the guideposts 72 of the lock 16 are seated within the slots 68, 40, 108 of the lid 14, tray 12 and push-rod 18 and, in particular, are aligned with the detents 109 and detent-slots 111. As such, the guideposts 72 prevent the detents 109 from causing the side-edges of the push-rod 18 to bow inward along the grooves 108 and becoming dislodged from the detent-slots 111 of the tray 12. Thus, the guideposts 72 of the lock 16 serve to lock the system 10 during shipping and storage by preventing lateral distal advancement of the push-rod 18.

Figure 9:
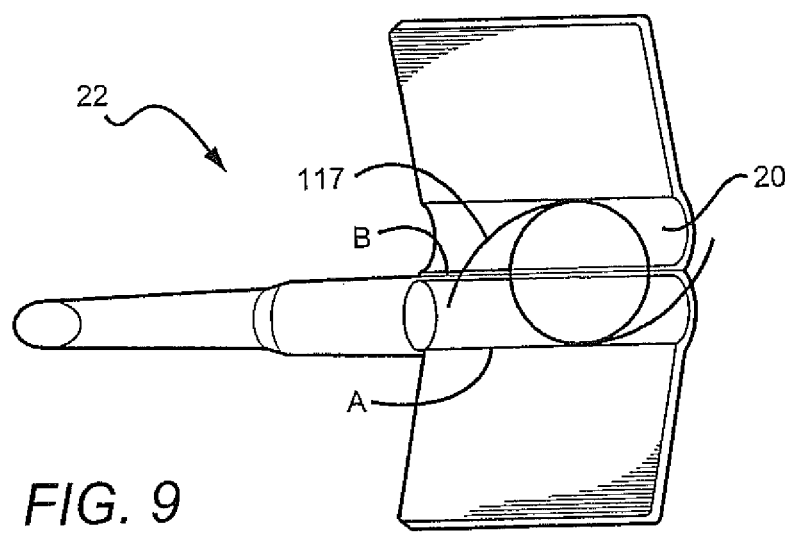
FIG. 9 is a perspective view of an IOL properly loaded within a lens cartridge in accordance with the present invention.

Proximal to the grooves 108 and located near the central, longitudinal axis of the slide 94 is an insertion member 110. The insertion member 110 includes a stabilizing segment 112 and a support segment 114, which are in stepped-relation to one another. In particular, the stabilizing segment 112 extends a certain length beyond the distal end of the support segment 114, thereby forming the stepped configuration. As best seen in FIG. 8, the stabilizing segment 112 includes a beveled or rounded distal tip 116 for supporting the proximal surface of the IOL 20 and controlling the rotational attitude of the IOL 20 during insertion into the loading zone 25 of the cartridge 22. As such, regardless of the initial positioning of the IOL 20 in the tray 12 of the device 10, during the delivery or transfer procedure, the insertion member 110 aids in advancing the IOL 20 into the cartridge 22 and controlling the IOL's rotational movement so that the IOL 20, and in particular the leading haptic 117 of the IOL 20, is correctly positioned (e.g., between points A and B, as shown in FIG. 9) within the cartridge 22.

Operation

Figure 10:
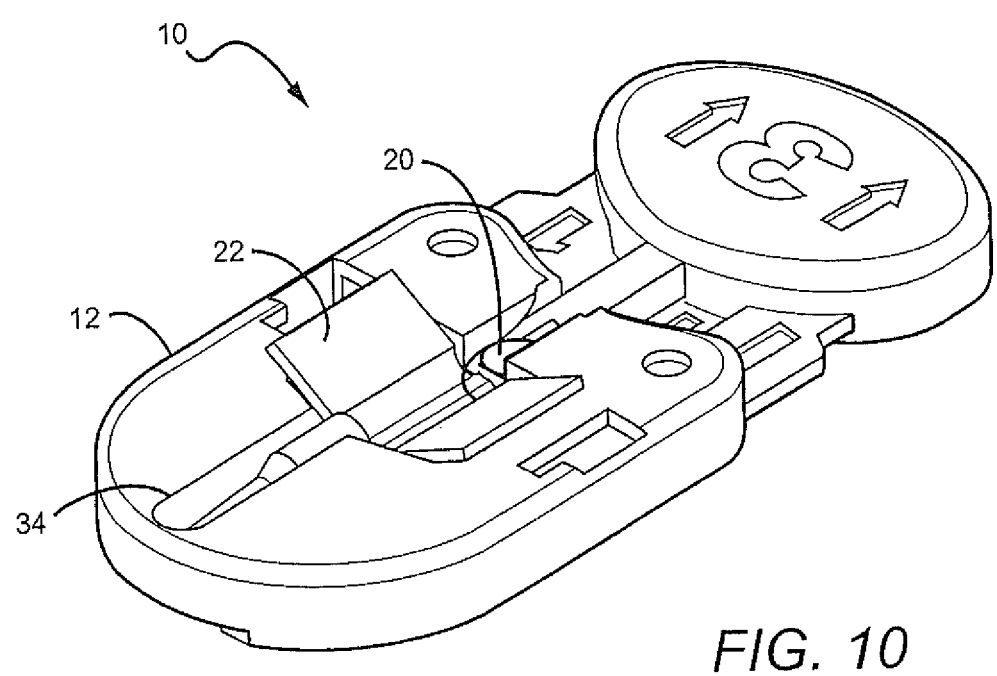
FIG. 10 illustrates an embodiment of a lens packaging system, with its lock and lid removed, prior to operation of the system in accordance with the present invention.

The packaging system 10 of the present invention is typically supplied to an end-user or surgeon with a lens cartridge 22 and IOL 20 pre-loaded within the center aperture 34 of the tray 12. FIG. 10 illustrates an embodiment of the packaging system as supplied to the end user with the lock 16 and lid 14 removed to clearly show the lens 20 and cartridge 22 within the device 10. Alternatively, the packaging system 10 may only include the IOL 20, thereby allowing the user of the device 10 to supply the cartridge 22.

Figure 11A:
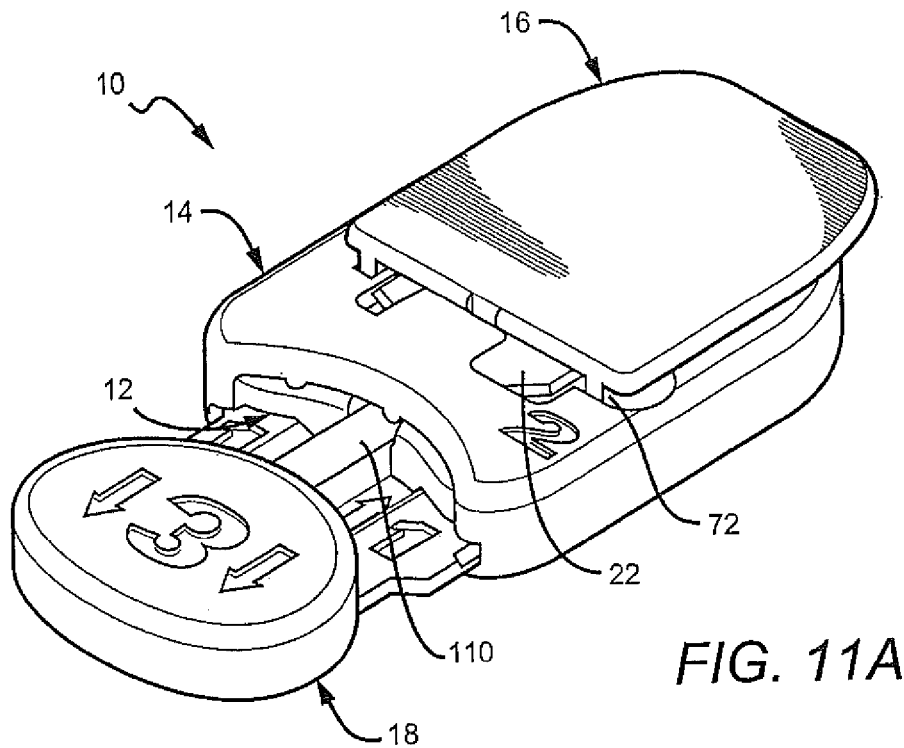
FIGS. 11A and 11B illustrate an embodiment of a lens packaging system prior to operation of the system in accordance with the present invention.
Figure 11B:
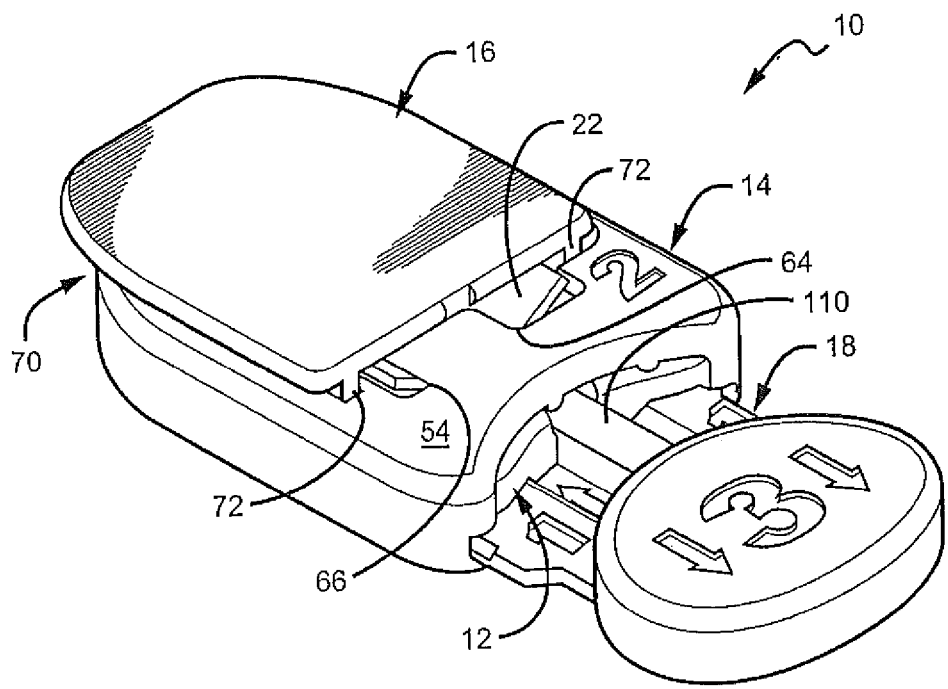

As shown in FIGS. 11A and 11B, prior to use, the tray 12 of the device 10 is covered with the lid 14. In addition, the push-rod 18 is an retracted or partially inserted position within the opening 46 of the tray 12 and the lock 16 is secured to the lid 14, tray 12 and push-rod 18, via the guide elements 72 and slots 40, 68, 108 (not shown), to prevent inadvertent or unintentional activation of the system 10. In particular, as described above, the guideposts or vertical members 72 of the lock 16 block further distal advancement of the push-rod 18, and its insertion member 110, until the lock 16 is removed from the system 10.

Figure 12A:
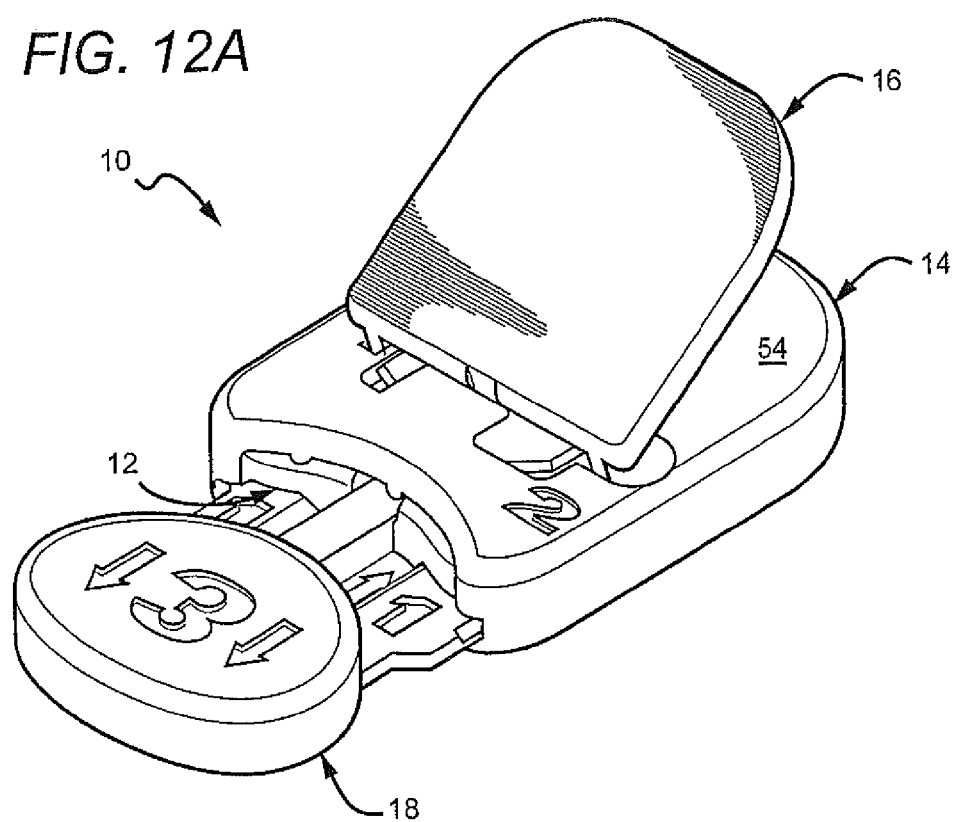
FIGS. 12A and 12B illustrate removal of the lock from an embodiment of a lens packaging system in accordance with the present invention.
Figure 12B:
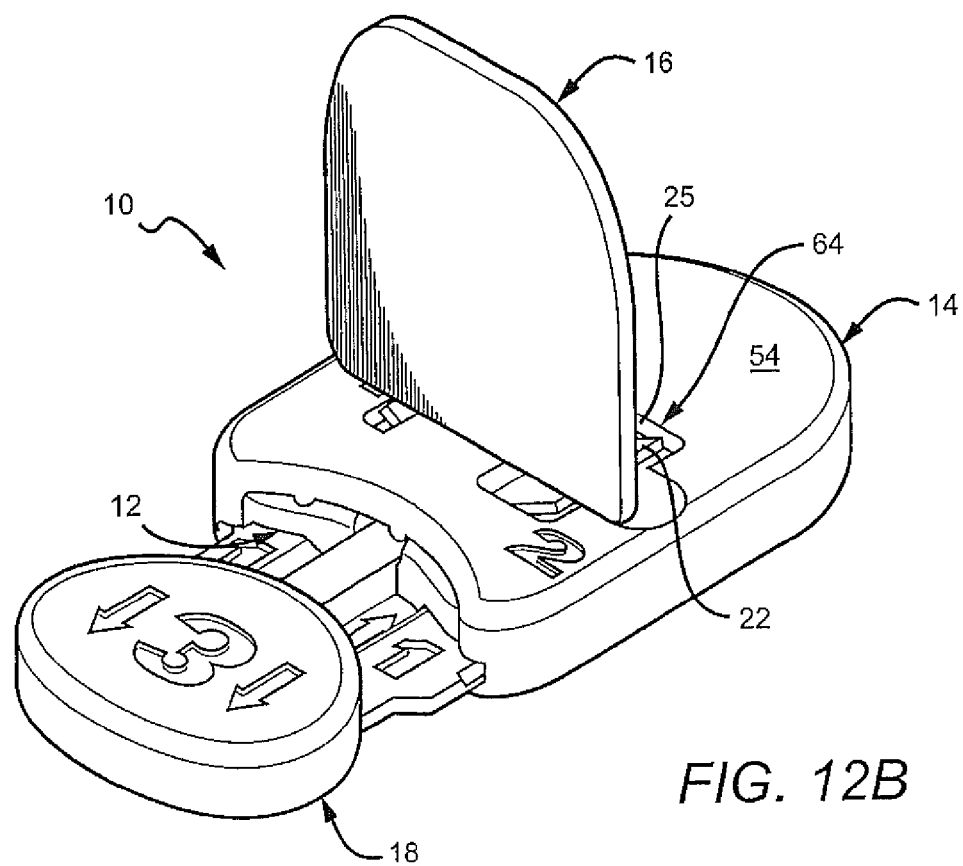
Figure 12C:
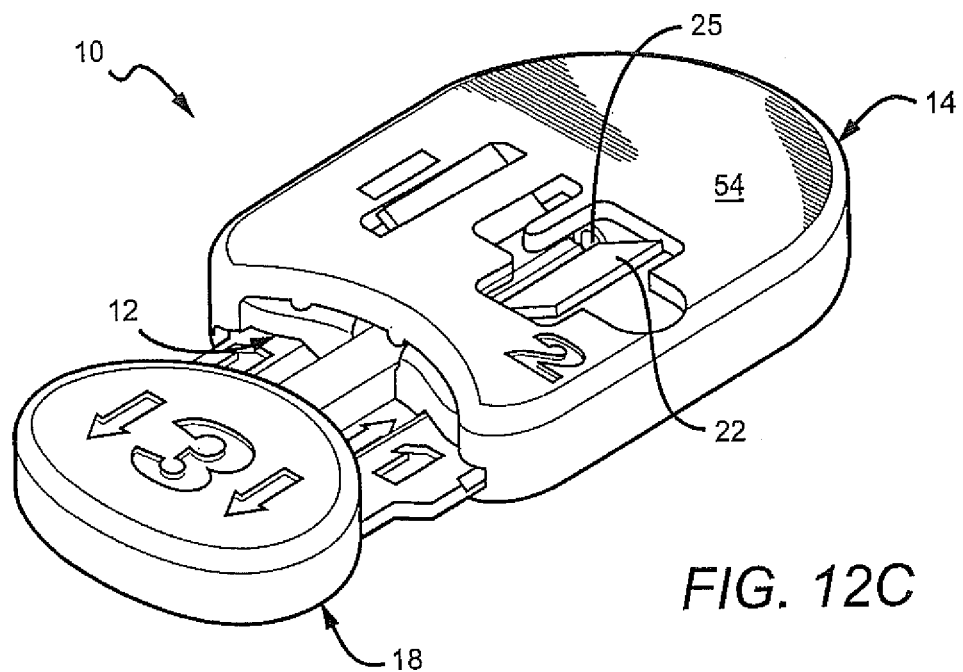
FIG. 12C illustrates an embodiment of a lens packaging system with its lock removed in accordance with the present invention.

During use of the device/system 10, the lock 16 is removed to expose the top surface 54 of the lid 14, as shown in FIGS. 12A and 12B. Preferably, the lid 14 is fabricated from a clear material to allow the user of the device 10 to inspect the system 10, particularly the lens cartridge 22 and IOL 20, prior to use to ensure that none of the components are damaged. Removal of the lock 16 also exposes the central window 64 of the lid 14 and, thereby, the loading zone 25 of the lens cartridge 22, as shown in FIG. 12C. Viscoelastic fluid is then applied to the loading zone 25 of the cartridge 22 and/or the edges of the IOL 22 through the opening 46 prior to device activation.

Figure 13A:
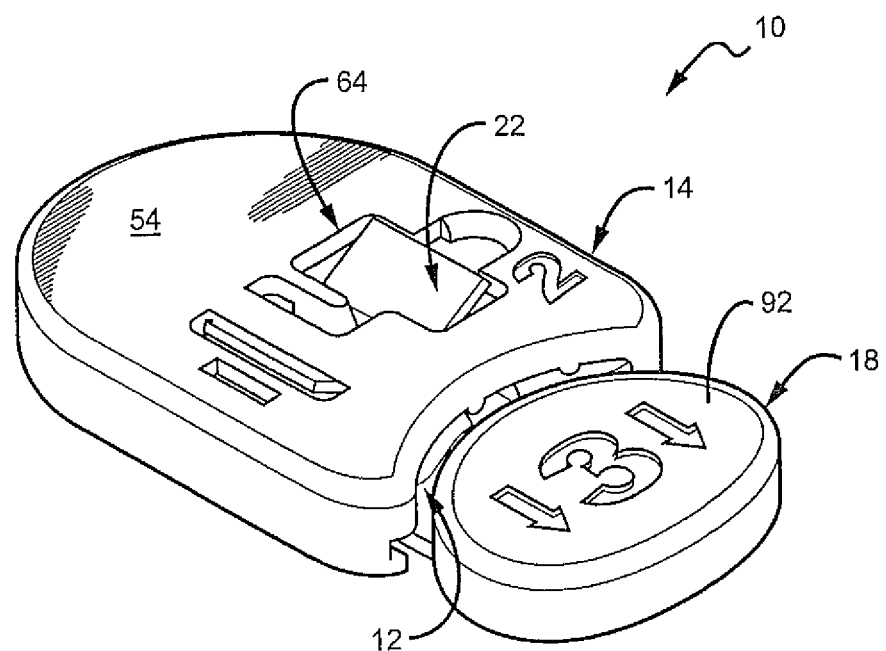
FIGS. 13A and 13B illustrate an embodiment of a lens packaging system with its push-rod distally advanced in accordance with the present invention.
Figure 13B:
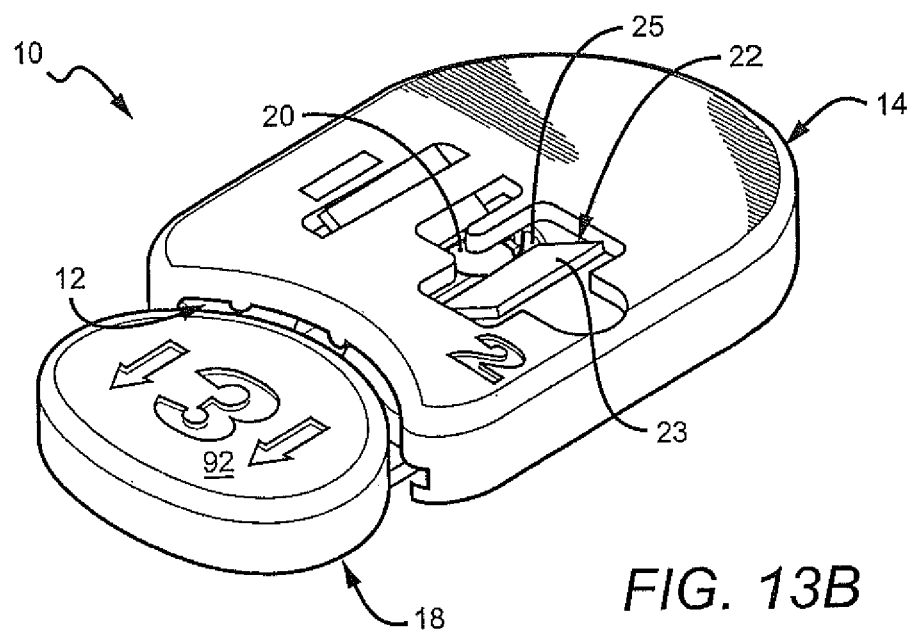

To activate the device 10, a user simply grasps the handle 92 of the push-rod 18 using, for example, his/her thumb and fore-finger, and pushes the push-rod 18 in a distal direction. Longitudinal sliding movement of the push-rod 18 causes the distal tip 116 of the insertion member 110 to push the IOL 20 along the longitudinal slot of the tray 12 and into the loading zone 25 of the cartridge 22, as shown in FIGS. 13A and 13B.

Figure 14:
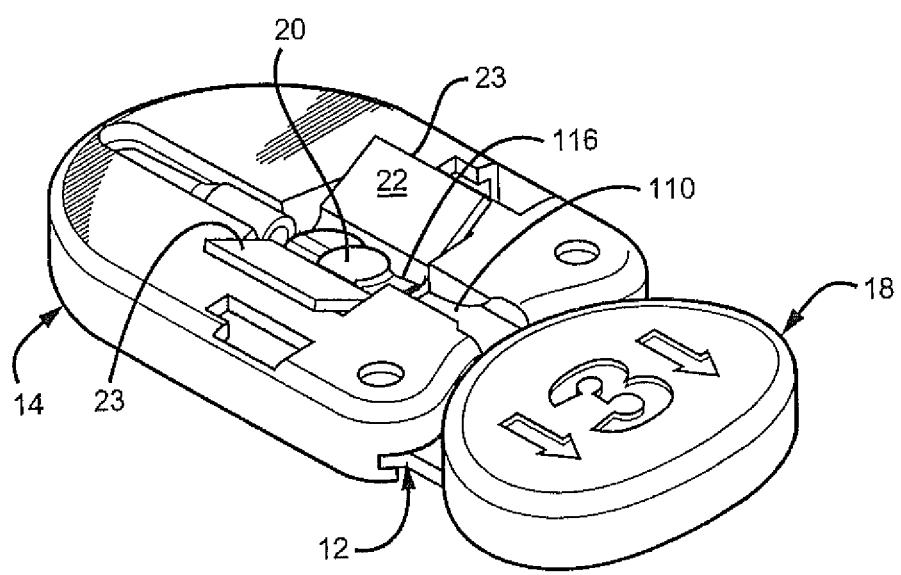
FIG. 14 illustrates an embodiment of a lens packaging system with its lid removed in accordance with the present invention.

After the push-rod 18 is fully advanced and the IOL 20 is properly positioned within the loading zone 25, the wing 23 of the cartridge 22 is partially folded to begin the folding/rolling of the IOL 20 within the loading zone 25. With the wing 23 of the cartridge 22 partially folded, the lid 14 of the packaging system 10 is then removed. As best seen in FIG. 14, the distal tip 116 of the insertion member 110 of the fully advanced push-rod 18 securely holds the loaded cartridge 22 within the tray 12 and prevents the cartridge 22 from falling out of the tray 12.

Figure 15:
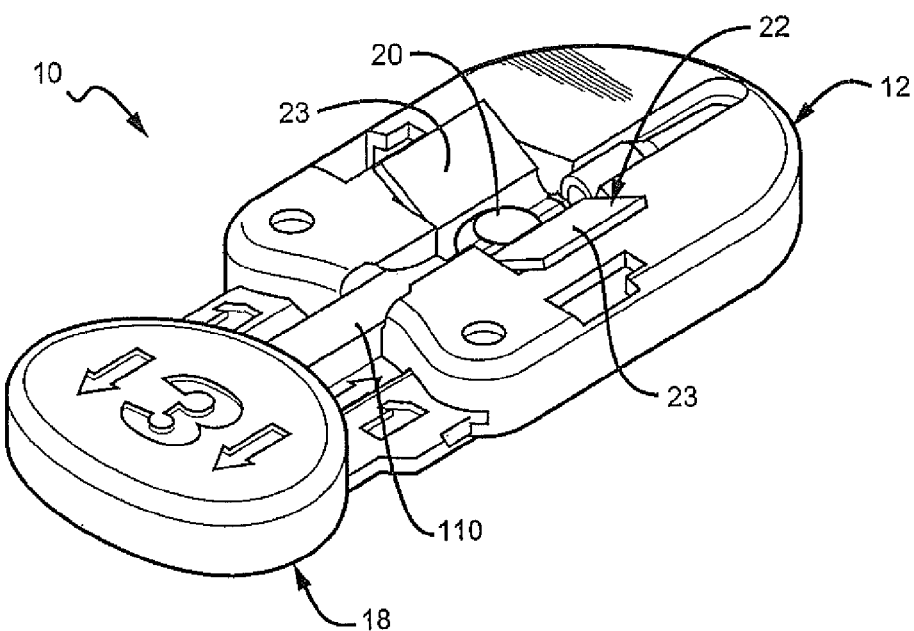
FIG. 15 illustrates an embodiment of a lens packaging system with its push-rod retracted in accordance with the present invention.
Figure 16:
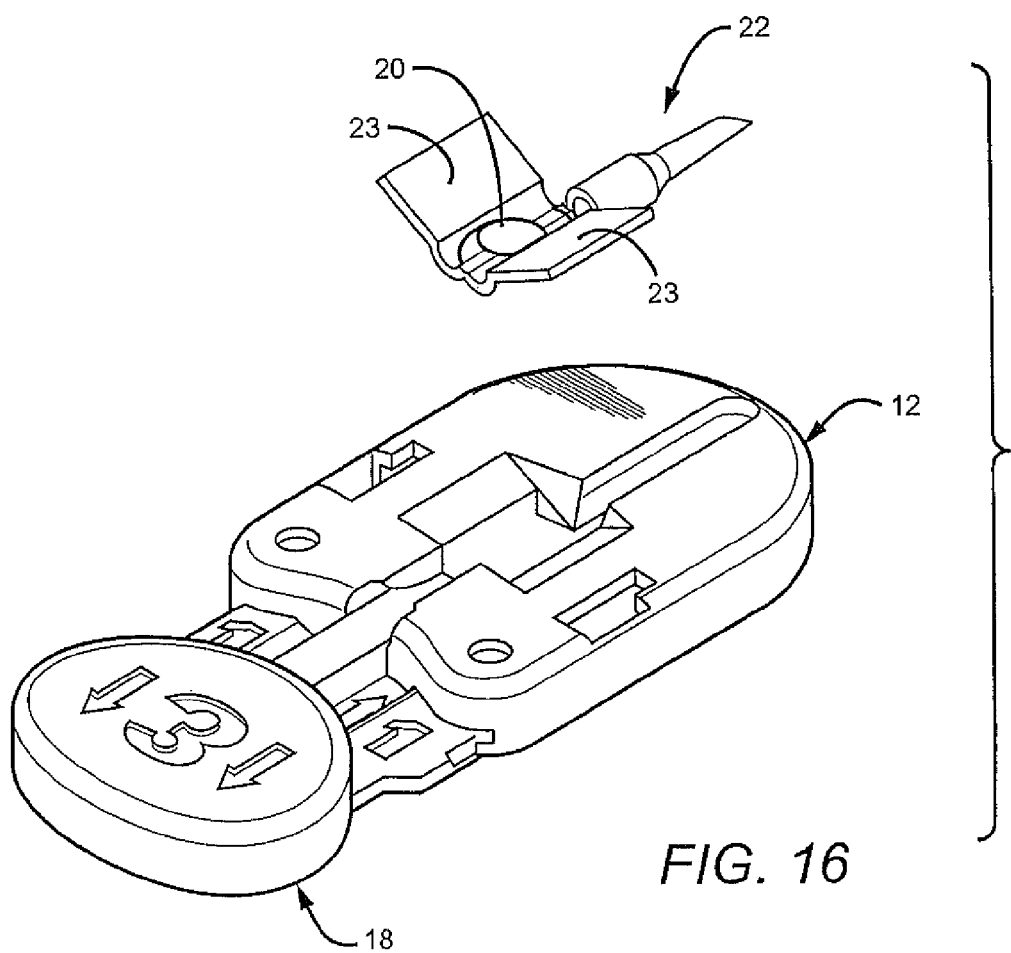
FIG. 16 illustrates removal of a loaded lens cartridge following operation of the system in accordance with the present invention.

Next, the push-rod 18 is proximally retracted to release the loaded cartridge 22 from the insertion member 110 of the push-rod 18, as shown in FIG. 15. The loaded cartridge 22 is then removed from the packaging system 10 (shown in FIG. 16) and its wings 23 maneuvered to a closed position, thereby completely rolling or folding the IOL 20 into the desired configuration. At this point, the user may easily transfer the cartridge 22 with its folded IOL 20 to an insertion device (not shown) for delivery of the IOL 20 into a patient's eye In view of the above, the packaging system 10 of the present invention and its method of operation simplify the removal and transfer of the IOL 20 to the IOL insertion device. In particular, the packaging device 10 enables a user to easily load an IOL 20 into a cartridge 22 without the use of forceps. The packaging device 10 also allows a user to fold and insert the IOL 20 into the cartridge 22 without damaging the IOL 20 and/or compromising IOL sterility. In addition, the related methods of operation minimize and/or eliminate the potential of damaging the IOL 20 during unpackaging, folding, transfer and/or loading procedures. Further, the device 10 and its method of use provide repeatable and consistent loading (e.g., with respect to position and rotation) of the IOL 20 into the cartridge 22.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A method of storing an intraocular lens and transferring said intraocular lens to a removable lens cartridge, having a pair of wings on either side of a loading zone, for use in a delivery device separate from the lens cartridge, the method comprising:

providing a packaging device housing said intraocular lens and said lens cartridge within a tray of said packaging device; wherein said packaging device further comprises: a push-rod comprised of a handle in communication with a push-rod slide; wherein the handle includes a top surface and a sidewall that extends around the perimeter of the top surface and wherein the push-rod slide includes a generally planar body, wherein the push rod is in communication with said tray; and a lock in communication with said tray and said push-rod, wherein said tray comprises a proximal end, a distal end, and an aperture, wherein said intraocular lens is housed within a first portion of said aperture and wherein a second portion of said aperture is configured to accommodate said lens cartridge in an unfolded position, the packaging device further including a lid surrounding and lying over a top of said tray and the lock being secured on top of the lid;

removing the packaging device from a sterile container for maintaining the intraocular lens in a sterile condition;

removing said lock to enable movement of said push-rod;

distally advancing said push-rod to distally transfer and secure said intraocular lens within the loading zone of said lens cartridge, the push-rod slide having a central insertion member that engages and pushes the intraocular lens into the loading zone, the insertion member having lateral edges that engage side walls of the lid and prevent upward movement of the lid from the tray prior to distal advancement and permit upward movement of the lid from the tray when the push-rod is distally advanced;

partially folding one of the pair of wings to begin folding said intraocular lens;

lifting the lid off the tray;

proximally retracting said push-rod to remove said push-rod from said lens cartridge, thereby permitting removal of said lens cartridge from said packaging device, said lens cartridge having said intraocular lens secured therein;

removing said lens cartridge from said packaging device, wherein said lens cartridge contains said intraocular lens;

maneuvering the pair of wings to a closed position; and wherein removing said lens cartridge causes said lens cartridge to be usable in connection with said delivery device.

2. The method of claim 1 wherein the lid side walls extend down around lateral side edges of said tray and form proximal notches to receive the lateral edges of the insertion member, and the lateral edges have indented sections that align with the lid side wall notches when the push-rod advances distally to permit upward movement of the lid from the tray.

3. The method of claim 2, wherein the lid comprises a clear material enabling a user to inspect underneath the lid.

4. The method of claim 1, wherein the push-rod slide is half-oval-shaped in the handle is oval shaped.

5. The method of claim 4, wherein the handle and the push-rod slide each have a width that is approximately the same.

6. The method of claim 1, further comprising adding viscoelastic into the loading zone.

7. The method of claim 1, wherein the lock includes vertical members that prevent movement of the lid, tray, and push-rod.

8. The method of claim 1, wherein the wings on either side of the loading zone are held open by the packaging device, and wherein the lid defines a window over one of the wings that permits a user to access and partially fold the wing.

9. The method of claim 8, wherein the wings of the lens cartridge may be fully folded to fold/roll the intraocular lens within the loading zone only after removal of the lid from the tray and retraction of the push-rod.

10. The method of claim 1, wherein the lock further includes an intraocular lens support that projects downward through the lid and engages a distal edge of the intraocular lens between the intraocular lens and the lens cartridge loading zone.

11. The method of claim 1, further including numerical actuation sequence indicators that convey to a user a sequence of operation for transferring the intraocular lens to the lens cartridge, including at least the number "1" visible on the insertion member.

12. A method of storing an intraocular lens and transferring the intraocular lens to a lens cartridge separate from and adapted to be received in and used by an intraocular lens insertion device, the method comprising:

providing a packaging device having a tray, a lid, a push-rod, and a lock, wherein the tray has a top surface with a central indentation for receiving and holding a lens cartridge and a proximal indentation sized to receive and hold an intraocular lens, the proximal indentation aligned with an elongated longitudinal slot that extends distally therefrom and receives and holds an injection tube of the lens cartridge, and wherein the lid fits closely over the tray and the lens cartridge and intraocular lens therein, the push-rod comprising a generally planar push-rod slide that extends from a proximal end of the tray longitudinally under and partly through the tray, the push-rod slide having lateral edges that engage side walls of the lid and prevent upward movement of the lid from the tray, and the lock is secured on top of the lid;

removing the packaging device from a sterile container for maintaining the intraocular lens in a sterile condition;

lifting the lock off of the lid, the lock having detents that fit within aligned detent slots in the lid and tray to prevent distal movement of the push-rod, wherein lifting the lock off of the lid permits movement of the push-rod;

sliding the push-rod in a distal direction, the push-rod slide having a central insertion member that engages and pushes the intraocular lens into a loading zone of the lens cartridge, the push-rod slide lateral edges being configured to permit upward movement of the lid from the tray when the push-rod is slid distally;

lifting the lid off the tray; and proximally retracting the push-rod to remove the push-rod from the lens cartridge, thereby permitting removal of the lens cartridge and intraocular lens therein from the packaging device for subsequent reception in and use by an intraocular lens insertion device.

13. The method of claim 12, wherein the lens cartridge includes a pair of wings on either side of the loading zone that are held open by the packaging device, the lid defining a window over one of the wings that permits a user to access and partially fold the wing.

14. The method of claim 13, wherein the wings of the lens cartridge may be fully folded to fold/roll the intraocular lens within the loading zone only after removal of the lid from the tray and retraction of the push-rod.

15. The method of claim 12, wherein the lid side walls extend down around lateral side edges of the tray and form proximal notches to receive the lateral edges of the push-rod slide, and the lateral edges have indented sections that align with the lid side wall notches when the push-rod slides in a distal direction to permit upward movement of the lid from the tray.

16. The method of claim 12, wherein the lid comprises a clear material enabling a user to inspect underneath the lid.

17. The method of claim 12, wherein the lid defines a window over the lens cartridge loading zone, and further comprising adding viscoelastic into the loading zone through the window prior to sliding the push-rod in a distal direction.

18. The method of claim 12, wherein the lock further includes an intraocular lens support that projects downward through the lid and engages a distal edge of the intraocular lens between the intraocular lens and the lens cartridge loading zone.

19. The method of claim 12, further including numerical actuation sequence indicators that convey to a user a sequence of operation for transferring the intraocular lens to the lens cartridge, including at least the number "1" visible on the push-rod slide.

* * * * *